US012667713B2

(12) United States Patent
Kerkhoffs et al.

(10) Patent No.: US 12,667,713 B2
(45) Date of Patent: Jun. 30, 2026

(54) BLOOD PUMP

(71) Applicant: Abiomed Europe GmbH, Aachen (DE)

(72) Inventors: Wolfgang Kerkhoffs, Aachen (DE); Ellen Keysselitz, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 848 days.

(21) Appl. No.: 17/911,198

(22) PCT Filed: Mar. 22, 2021

(86) PCT No.: PCT/EP2021/057186
§ 371 (c)(1),
(2) Date: Sep. 13, 2022

(87) PCT Pub. No.: WO2021/191106
PCT Pub. Date: Sep. 30, 2021

(65) Prior Publication Data
US 2023/0105131 A1 Apr. 6, 2023

(30) Foreign Application Priority Data
Mar. 27, 2020 (EP) ..................................... 20166343

(51) Int. Cl.
*A61M 60/824* (2021.01)
*A61M 60/13* (2021.01)
(Continued)

(52) U.S. Cl.
CPC .......... *A61M 60/824* (2021.01); *A61M 60/13* (2021.01); *A61M 60/221* (2021.01); *A61M 60/422* (2021.01); *A61M 60/806* (2021.01)

(58) Field of Classification Search
CPC .............. A61M 60/824; A61M 60/806; A61M 60/221; A61M 60/13; A61M 60/422
See application file for complete search history.

(56) References Cited

U.S. PATENT DOCUMENTS

| | | | |
|---|---|---|---|
| 5,851,174 A | 12/1998 | Jarvik et al. | |
| 5,951,263 A * | 9/1999 | Taylor ................. | A61M 60/827 417/423.12 |

(Continued)

FOREIGN PATENT DOCUMENTS

| | | |
|---|---|---|
| CN | 101715352 A | 5/2010 |
| CN | 107921187 A | 4/2018 |

(Continued)

OTHER PUBLICATIONS

Extended European Search Report from corresponding European Patent Application No. 20166343.2 dated Sep. 29, 2020 (8 pp.).
(Continued)

*Primary Examiner* — Amanda L Steinberg
(74) *Attorney, Agent, or Firm* — BOTOS CHURCHILL IP LAW LLP

(57) ABSTRACT

This invention relates to an intravascular blood pump, comprising a pumping device with a pump section and a drive section, wherein the pump section comprises a pump casing having a primary blood flow inlet and a primary blood flow outlet hydraulically connected by a primary passage and the drive section comprises a stator and a rotor rotatable about an axis of rotation and configured to rotate a primary impeller, the primary impeller being configured to convey a primary blood flow from the primary blood flow inlet to the primary blood flow outlet along the primary passage, the drive section further comprises an ancillary blood flow inlet and an ancillary blood flow outlet hydraulically connected by an ancillary passage extending through an axial gap between the rotor and the stator and an ancillary impeller arranged at a drive section end (DSE) of the rotor and rotatable about the axis of rotation along with the rotor, the ancillary impeller comprising one or more ancillary impeller vanes configured to convey an ancillary blood flow (ABF) from the ancillary blood flow inlet to the ancillary
(Continued)

blood flow outlet along the ancillary passage in a direction toward a pump section end (PSE) of the pumping device, and the rotor is mounted in a blood-purged radial sliding rotor bearing with an inner rotor bearing surface and an outer rotor bearing surface, and the ancillary impeller forms the inner rotor bearing surface of the radial sliding rotor bearing.

35 Claims, 8 Drawing Sheets

(51) Int. Cl.
| | | |
|---|---|---|
| *A61M 60/221* | (2021.01) | |
| *A61M 60/422* | (2021.01) | |
| *A61M 60/806* | (2021.01) | |

(56) References Cited

U.S. PATENT DOCUMENTS

| | | | | |
|---|---|---|---|---|
| 2010/0174131 A1* | 7/2010 | Foster | ................. | A61M 60/824 |
| | | | | 600/16 |
| 2014/0341726 A1* | 11/2014 | Wu | ........................... | F04D 1/04 |
| | | | | 415/209.1 |
| 2017/0087286 A1* | 3/2017 | Spanier | ............... | A61M 60/824 |
| 2018/0228953 A1* | 8/2018 | Siess | ................... | A61M 60/422 |
| 2019/0282744 A1 | 9/2019 | D'Ambrosio et al. | | |

FOREIGN PATENT DOCUMENTS

| | | |
|---|---|---|
| EP | 1727987 B1 | 12/2016 |
| EP | 3127562 A1 | 2/2017 |
| JP | 2010528797 A | 8/2010 |
| JP | 2018528804 A | 10/2018 |
| KR | 20180037203 A | 4/2018 |
| TW | 201221161 A | 6/2012 |
| WO | 2008152425 A1 | 12/2008 |

OTHER PUBLICATIONS

International Search Report and Written Opinion from International Application Application No. PCT/EP2021/057186 dated Jun. 22, 2021 (12 pp.).

Office Action from corresponding Japanese Patent Application No. 2022-558129 dated Dec. 10, 2024 (11 pp.).

First Office Action for corresponding Chinese Application No. 202180025290.3 dated Jan. 3, 2025 (23 pgs.).

Office Action from corresponding Israeli Patent Application No. 323207 dated Feb. 2, 2026 (4 pp.).

Office Action from corresponding Korean Patent Application No. 10-2022-7037734 dated Dec. 18, 2025 (14 pp.).

* cited by examiner

BLOOD PUMP

CROSS REFERENCE TO RELATED APPLICATIONS

The present application is a national phase entry under 35 U.S.C. § 371 of International Application No. PCT/EP2021/057186 filed Mar. 22, 2021, published in English, which claims priority from European Patent Application No. 20166343.2 filed Mar. 27, 2020, all of which are incorporated herein by reference.

TECHNICAL FIELD OF THE INVENTION

This invention relates to an intravascular blood pump to support or replace the function of the heart by creating an extra blood flow in a patient's blood vessel.

BACKGROUND OF THE INVENTION

Blood pumps of different types are known such as axial blood pumps, centrifugal blood pumps and mixed-type or diagonal blood pumps, where the blood flow is caused by both axial and radial forces. Intravascular blood pumps are usually inserted percutaneously, such as through the femoral artery into the left ventricle so as to bridge the aortic valve or through the femoral vein into the right ventricle.

A rotary blood pump has an axis of rotation. In this patent application, the terms "radial" and "axial" refer to the axis of rotation and mean "in radial direction in relation to the axis of rotation" and "along the axis of rotation", respectively. The term "inner" means radially toward the axis of rotation, and the term "outer" means radially away from the axis of rotation.

An intravascular blood pump typically comprises a pumping device as a main component. The pumping device has a pump section including a primary impeller for pumping the blood from a blood flow inlet to a blood flow outlet and a drive section including a motor for driving the primary impeller. The pump section may include a flexibly bendable cannula between the blood flow inlet and outlet.

The pumping device comprises a pump section end which is arranged at a pump side of the pumping device. The pumping device further comprises a drive section end which is arranged at a drive side of the pumping device. The blood pump may further comprise a catheter connected to the pumping device in order to supply the pumping device e.g. with energy, and/or a purge fluid. The catheter may be connected to the pump section end but is mostly connected to the drive section end of the pumping device. It is also conceivable to rotate the impeller in a forward and in a reverse direction. Then, the blood flow inlet and the blood flow outlet of the pump section may interchange.

Usually, the impeller is supported within the pumping device by means of at least one impeller bearing. Different rotor bearing types are known, such as sliding bearings, in particular hydrodynamic sliding bearings, pivot bearings, hydrostatic bearings, ball bearings etc., and combinations thereof. In particular, contact-type bearings may be realized as "blood immersed bearings", where the bearing surfaces have blood contact. Problems during operation may be friction and heat. In case of a blood immersed bearing, a further problem may be blood clotting due to heat or not enough rinse.

An example of a blood-purged radial sliding bearing is disclosed in WO 2017/021465. FIG. 33 of this document discloses an impeller device comprising a generally cylindrical primary impeller. Primary impeller vanes of the primary impeller extend toward an axis of rotation of the primary impeller. The tips of the primary impeller vanes form an outer rotor bearing surface of a sliding bearing. A cylindrical surface of a pin which is arranged at the center of the primary impeller forms the inner rotor bearing surface of the sliding bearing. In order to cool a rotor and a stator of a drive unit, an ancillary impeller is provided at a side of the drive unit opposite to the primary impeller and is rotatable with the rotor. The ancillary impeller pumps blood into an axial gap between the stator and the rotor. At an axial end of the ancillary impeller, a sliding bearing between inner ends of the ancillary impeller and a bearing pin is arranged. This construction requires much axial construction space and thus leads to a voluminous blood pump which is difficult to advance in a blood vessel.

SUMMARY OF THE INVENTION

It is an object of the present invention to provide a compact blood pump with a blood flow through the axial gap between the stator and the rotor.

This is achieved according to the present invention by a blood pump having the features of independent claim 1. Preferred embodiments and further developments of the invention are specified in the claims dependent thereon.

According to a first aspect of the invention, an intravascular blood pump comprises a pumping device with a pump section and a drive section. The pump section comprises a pump casing having a primary blood flow inlet and a primary blood flow outlet which are hydraulically connected by a primary passage. The drive section comprises a stator and a rotor which is rotatable about an axis of rotation and configured to rotate a primary impeller. The primary impeller is configured to convey a primary blood flow from the primary blood flow inlet to the primary blood flow outlet along the primary passage. The drive section further comprises an ancillary blood flow inlet and an ancillary blood flow outlet which are hydraulically connected by an ancillary passage such that an ancillary blood flow is conveyable from the ancillary blood flow inlet to the ancillary blood flow outlet along the ancillary passage. The ancillary passage includes an axial gap extending between the rotor and the stator. The axial gap is preferably also a magnetic gap of an electric motor comprising the stator and the rotor. Further provided is an ancillary impeller arranged at the drive section end of the rotor, which is rotatable about an axis of rotation along with the primary impeller and comprises one or more ancillary impeller vanes configured to convey the ancillary blood flow through the ancillary passage. Further, the blood pump comprises a blood-purged radial sliding bearing for bearing the rotor. The radial sliding rotor bearing comprises an inner rotor bearing surface and an outer rotor bearing surface. The ancillary impeller forms the inner rotor bearing surface of the radial sliding rotor bearing. Thus, the blood-purged sliding bearing of the ancillary impeller is arranged radially outward from the ancillary impeller. This way, an axially compact blood pump can be built.

Preferably, the blood-purged radial sliding rotor bearing is arranged close to an outer circumference of the pump casing such that thermal conduction from the outer rotor bearing surface through the pump casing outward to a surrounding general blood stream can take place. This may further help to build a compact and reliable blood pump in which heat is effectively transported away. This may also help to deliver cooler blood to the axial gap.

Preferably, the ancillary impeller is a radially or radially-axially delivering impeller. Thus, the ancillary impeller generates centrifugal forces in the ancillary blood flow to generate pressure.

Preferably, the inner rotor bearing surface formed by the ancillary impeller and the rotor have a common outer diameter. Then, the ancillary blood flow can enter the axial gap without significant deflection. Furthermore, in regard to the fact that an intravascular blood pump must have a small outer diameter as it has to be advanced through blood vessels up to the heart, the construction space in radial direction is optimally utilized by the feature of a common outer diameter of the inner rotor bearing surface and the rotor. That is, the pressure in the blood entering the axial gap is increased by the ancillary impeller up to the limits, limited only by the radial construction space at the drive section end of the blood pump.

Preferably, at least two, more preferably at least three ancillary impeller vanes extend up to the outer rotor bearing surface. The respective surfaces of the ancillary impeller vanes closest to the outer rotor bearing surface form together the inner rotor bearing surface. This is the surface of the ancillary impeller which mounts the rotor relative to the outer rotor bearing surface. Thus, the inner rotor bearing surface is discontinuous and comprises at least two, preferably at least three, separate sections defined by the tip ends of the impeller vanes. In this way, the tips of the ancillary impeller vanes can form one part of a radial sliding rotor bearing. The outer rotor bearing surface may be a single continuous surface. Further in the alternative, the outer rotor bearing surface may have grooves and/or slots.

Preferably, at least one ancillary impeller vane protrudes from the ancillary impeller in an axial direction in regard to the axis of rotation. In this way, the vanes can form an axial end of the rotating part of the blood pump. This axial end may be open to let blood flow into the ancillary impeller.

Preferably, a radial outer edge of at least one ancillary impeller vane is chamfered. A corresponding chamfer may be arranged between a section of an ancillary impeller vane extending in an axial direction and a section of an ancillary impeller vane extending in a radial direction in regard to the axis of rotation. Particularly, the blood pump may comprise a tapered section axially between the supply catheter and the pump casing with larger diameter. The taper facilitates advancement of the pump through a blood vessel. Preferably, the chamfer of the ancillary impeller is arranged beneath the tapered section. This way, the chamfer enables to build a more compact blood pump.

Preferably, at least one ancillary vane forms an ancillary pump gap with an inner wall of the pump casing or with a further part arranged inside thereof. The ancillary pump gap preferably has a radial outer border which extends axially and forms a part of the radial sliding rotor bearing. It is preferred that the ancillary pump gap further has a radially extending axial end portion arranged between at least one ancillary impeller vane and an inner wall of the pump casing, preferably at a chamfered end of a radially extending end surface of the vane. The radially extending portion of the pump gap keeps up the pressure which is built up by the ancillary impeller vanes. Forming this gap in an axial-radial direction such as along a chamfer helps to build a compact blood pump. Particularly, the pump casing can be tapered at the position of the chamfer.

Preferably, at least one, most preferably all ancillary impeller vanes are straight in the direction of their radial extension. It is preferred that at least one, preferably all ancillary impeller vanes extend approximately or exactly along a radial direction in regard to the axis of rotation, or inclined to this direction. The pumping effect of ancillary impeller vanes that extend along the radial direction is independent of the sense of rotation of the ancillary impeller. Straight ancillary impeller vanes of the ancillary impeller tend to cause less blood clotting.

It is preferred that the outer circumferential surface of at least two, preferably at least three, ancillary impeller vanes has a slant rising in radial direction in regard to the axis of rotation along a circumferential direction of the ancillary impeller. In this way, a hydrodynamic sliding rotor bearing can be formed by the tip of the vanes in combination with a generally ring-shaped outer rotor bearing surface. The slant is configured such that, in a direction of rotation, a pressure buildup in a bearing gap of the hydrodynamic sliding rotor bearing is achieved. The slant may slant along the whole width of the ancillary impeller vane along its circumferential direction. Alternatively, it is also possible to provide two slants in opposite direction starting from opposite ends of a tip of an ancillary impeller vane along the circumference of the ancillary impeller such that a maximum radial rising of the ancillary impeller vane is achieved in an intermediate section of a part of the tip of the ancillary impeller vane. Such an impeller is operable in two opposite directions of rotation. Equivalent constructional details may additionally or alternatively be provided in the outer impeller bearing surface.

It is preferable to apply the aforementioned specifications of the outer circumferential surface to an axial or radial-axial end surface of an ancillary impeller vane. An end surface of the ancillary impeller vane may extend in a radial direction in regard to the axis of rotation or extend along a chamfer arranged at an edge of the ancillary impeller vane. The aforementioned types of hydrodynamic end surfaces of the ancillary impeller vanes may be realized in bearing surfaces of an inner axial sliding rotor bearing or axial-radial sliding rotor bearing between the ancillary impeller and a non-rotating part of the blood pump, such as the pump casing. An outer axial or axial-radial rotor bearing surface of the axial sliding rotor bearing may, for example, be arranged at the pump casing. With the axial or axial-radial rotor bearing, axial forces of the impeller can be transferred.

Preferably, the axial or axial-radial rotor bearing surface is made of a ceramic material. For example, the ceramic material can be provided as a ceramic coating. Alternatively, the corresponding sections of the impeller and/or the pump casing may be entirely made of ceramic material.

Preferably, a radially protruding bulge is arranged at the outer and/or at the inner rotor bearing surface with the apex of the bulge extending in a circumferential direction. The bulge may extend on the outer or inner rotor bearing surface. Preferably, the radius of the apex is greater than one tenth of the diameter of the ancillary impeller. Such a protruding bulge has the advantage that, in case that the rotating part of the blood pump swivels transversely to the main rotation direction, no sharp edges at an end of the rotating part touches a surrounding non-rotating part, which would otherwise damage the pump surface. Instead, only the protruding bulge contacts the non-rotating counter-surface. Therefore, the risk of damaging the rotor bearing because of a swiveling axis of rotation is reduced.

Preferably, the inner rotor bearing surface is made of a ceramic material. For example, the inner rotor bearing surface can be provided as a ceramic coating. The hardness of a ceramic material improves the wear characteristics of the inner rotor bearing surface. Preferably, the ceramic material is inert in regard to reactions with the blood.

Preferably, the ancillary impeller is an integral piece of ceramic material. It is also possible that the ancillary impeller is made of a non-ceramic material which is coated with a ceramic material.

Preferably, also the outer rotor bearing surface is made of a ceramic material. For example, the outer rotor bearing surface can be provided as a ceramic coating.

Preferably, the pumping device comprises a specific component forming the outer rotor bearing surface of ceramic material, such as a rotor bearing ring. A separate ceramic component provides a good form stability of the outer rotor bearing surface, which is especially important because of the small inner rotor bearing surface and increased surface pressures at the tips of the ancillary impeller vanes.

Preferably, the ceramic material is silicon carbide. Silicon carbide has the advantage of a great thermal conductivity in comparison to most other ceramic materials. Thus, heat can effectively be transferred away from a sliding rotor bearing. The heat conduction may occur through the rotor toward the impeller or through the pump casing, for example, especially through the rotor bearing ring.

Preferably, an axial length of the ancillary impeller is smaller than a maximum outer diameter of the ancillary impeller. In this way, the ancillary impeller does not overly extend along the axis of rotation but is a narrow component in the blood pump. The pumping effect is then generated mainly in a radial direction, which is more effective than in the axial direction. This is advantageous for building a compact blood pump.

Preferably, the primary impeller is arranged at a side of the rotor which is opposite to the side of the rotor where the ancillary impeller is arranged. This arrangement has the advantage that a bearing at an end of the rotating parts of the blood pump, such as a radial sliding bearing at the ancillary impeller, optimally mounts the rotating parts in regard to stiffness against swiveling of the axis of rotation.

Preferably, the ancillary blood flow outlet is arranged outside of the primary passage of the primary impeller. Thus, the ancillary blood flow is separated from the primary blood flow. Then, blood conveyed via the ancillary passage only mixes with blood from the primary passage outside of the primary passage. This creates less hydraulic losses as the blood flows have opposite flow directions, and it makes the ancillary blood flow independent of the primary blood flow, which is dependent upon pre- and afterload conditions. In other words, due to the separation of the primary blood flow from the ancillary blood flow, the latter is merely contingent on the pump rotation.

Preferably, the ancillary blood flow outlet is arranged obliquely or perpendicularly to a direction of a main blood flow delivered by the pump section. When the main blood flow flows adjacent to the ancillary blood flow outlet, then blood will be sucked from the ancillary blood flow outlet by the Venturi effect. This supports the ancillary blood flow.

Preferably, the ancillary blood flow inlet comprises a plurality of inlet holes. The inlet holes are preferably arranged circumferentially about the axis of rotation. Preferably, the inlet holes are arranged in a circle. It is further preferred that in an interspace between two neighboring ones of the inlet holes, a wire channel is arranged. For example, the wire channel can be utilized for accommodating at least one electric supply wire for the drive unit. Such an arrangement of inlet holes and wire channels make up for a compact design of the blood pump.

The axial gap between the rotor and stator is arranged downstream of the ancillary impeller. The ancillary impeller may be arranged in a cavity between the ancillary blood flow inlet and the axial gap. In particular, the ancillary impeller conveys blood radially or radially-axially. Along the ancillary blood flow passage, downstream of the ancillary blood flow inlet, an ancillary inlet through-hole is arranged in the wall of the pump casing. From the ancillary inlet through-hole, the blood can enter the cavity at an internal end of the ancillary inlet through-hole. The internal end of the ancillary inlet through-hole is preferably arranged further radially inward than the axial gap. Centrifugal forces which are active between an inner region of the ancillary impeller and an outer region of the ancillary impeller generate pressure to convey the blood through the axial gap. Especially, a radial outermost section of the ancillary blood flow inlet may be arranged further radially inward than a radially innermost section of an inlet into the axial gap.

Preferably, the pumping device further comprises a tertiary impeller. The tertiary impeller is preferably arranged downstream of the axial gap. It is preferred that the tertiary impeller is configured to draw blood out of the axial gap. The tertiary impeller thus increases the throughput of blood through the ancillary passage.

It is preferred that the tertiary impeller is rotatable about the axis of rotation. The tertiary impeller may be rotatable along with the rotor.

Preferably, the ancillary blood flow outlet is arranged at a radial gap formed between the primary impeller and the stator. It is preferred that blood can flow out of the radial gap all over an outer circumferential cross section of the radial gap. Such a large outflow cross section reduces the hydraulic resistance of the ancillary blood passage.

Particularly, a rotatable wall of the radial gap is rotatable along with the rotor. Thus, a spiral drag flow of blood is created which, by its rotation inside the gap, enhances the blood flow through the ancillary passage by centrifugal forces on the blood in the spiral drag flow.

Preferably, a stationary wall of the radial gap is arranged opposite to the rotatable wall of the radial gap. The stationary wall is preferably mechanically connected to the stator.

Preferably, the tertiary impeller is arranged inside the radial gap. Preferably, the tertiary impeller forms part of the rotatable wall of the radial gap. It is preferred that the tertiary impeller comprises at least one tertiary impeller vane. The tertiary impeller vane is preferably configured to convey blood in a radial direction. The tertiary impeller vane may extend approximately or exactly in the radial direction in regard to the axis of rotation. Then, the effect of the tertiary impeller is independent of the sense of rotation of the tertiary impeller.

Preferably, an inflow into the tertiary impeller is arranged at an outflow end of the axial gap. Thus, the tertiary impeller advantageously draws blood directly from the axial gap. A short connection between the axial gap and the radial gap reduces the hydraulic resistance along the ancillary blood flow passage.

BRIEF DESCRIPTION OF THE DRAWINGS

The aforegoing summary as well as the following detailed description of preferred embodiments will be better understood when read in conjunction with the appendant drawings. The scope of the disclosure is not limited, however, to the specific embodiments disclosed in the drawings. In the drawings:

FIG. 2 shows a part of FIG. 1 with the pump section in an enlarged view, FIG. 4 shows a perspective view toward the pump section end of the first embodiment of the blood pump, FIG. 5 essentially shows the view of FIG. 4, but with a transparent pump casing, FIG. 6 essentially shows the same view as FIG. 5, but of a second embodiment of the blood pump.

DETAILED DESCRIPTION

Figure 1:
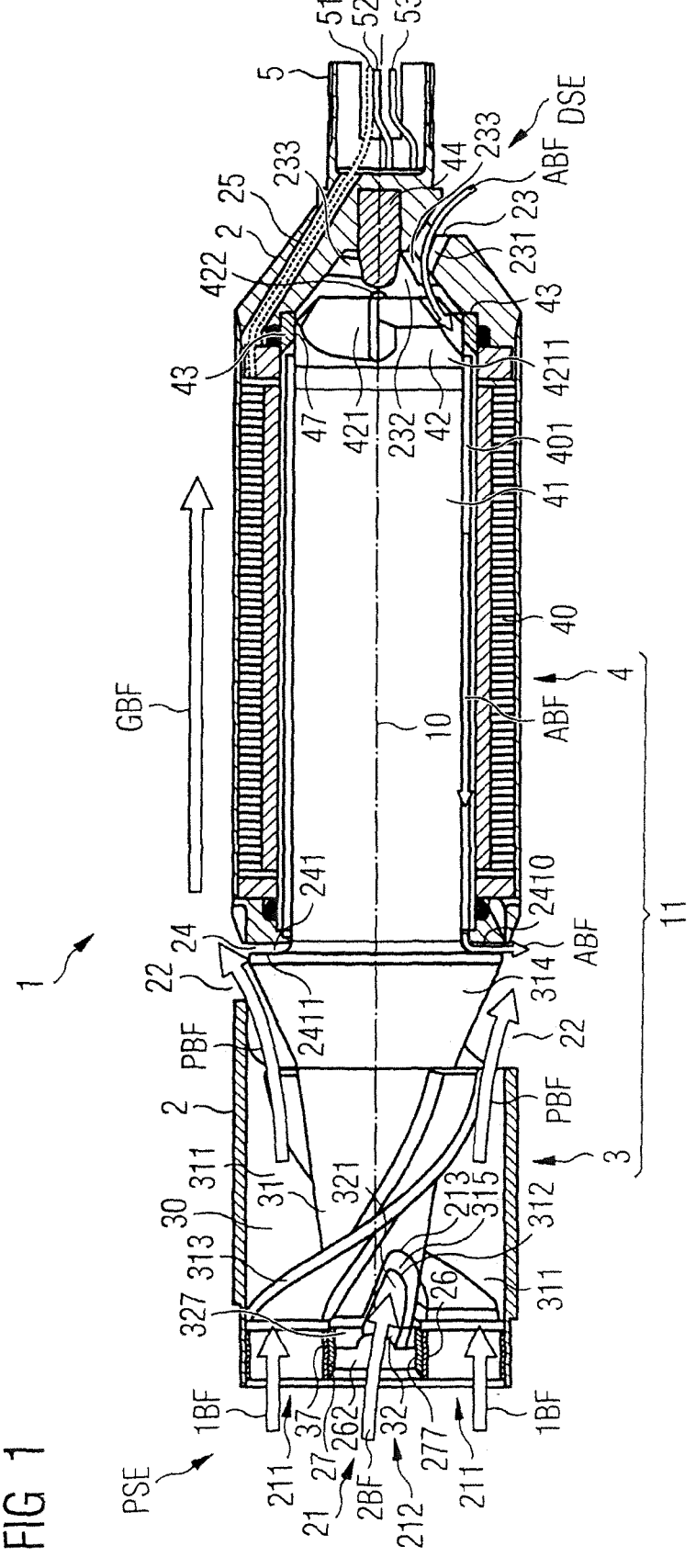
FIG. 1 shows a cross section of a first embodiment of a blood pump according to the invention.

In FIG. 1, a cross sectional view of a first embodiment of an intravascular blood pump is illustrated. Rotating parts are not shown cut. The intravascular blood pump 1 comprises a pumping device 11 and a supply line in the form of a catheter 5 attached thereto.

The pumping device 11 comprises a pump casing 2 of substantially cylindrical form, at least in an intermediate section thereof. The pump casing 2 comprises a blood flow inlet 21 and a blood flow outlet 22. In FIG. 1, the pump casing 2 seems to comprise two separate sections, but these sections are either integral or connected to form a single piece.

Figure 2:
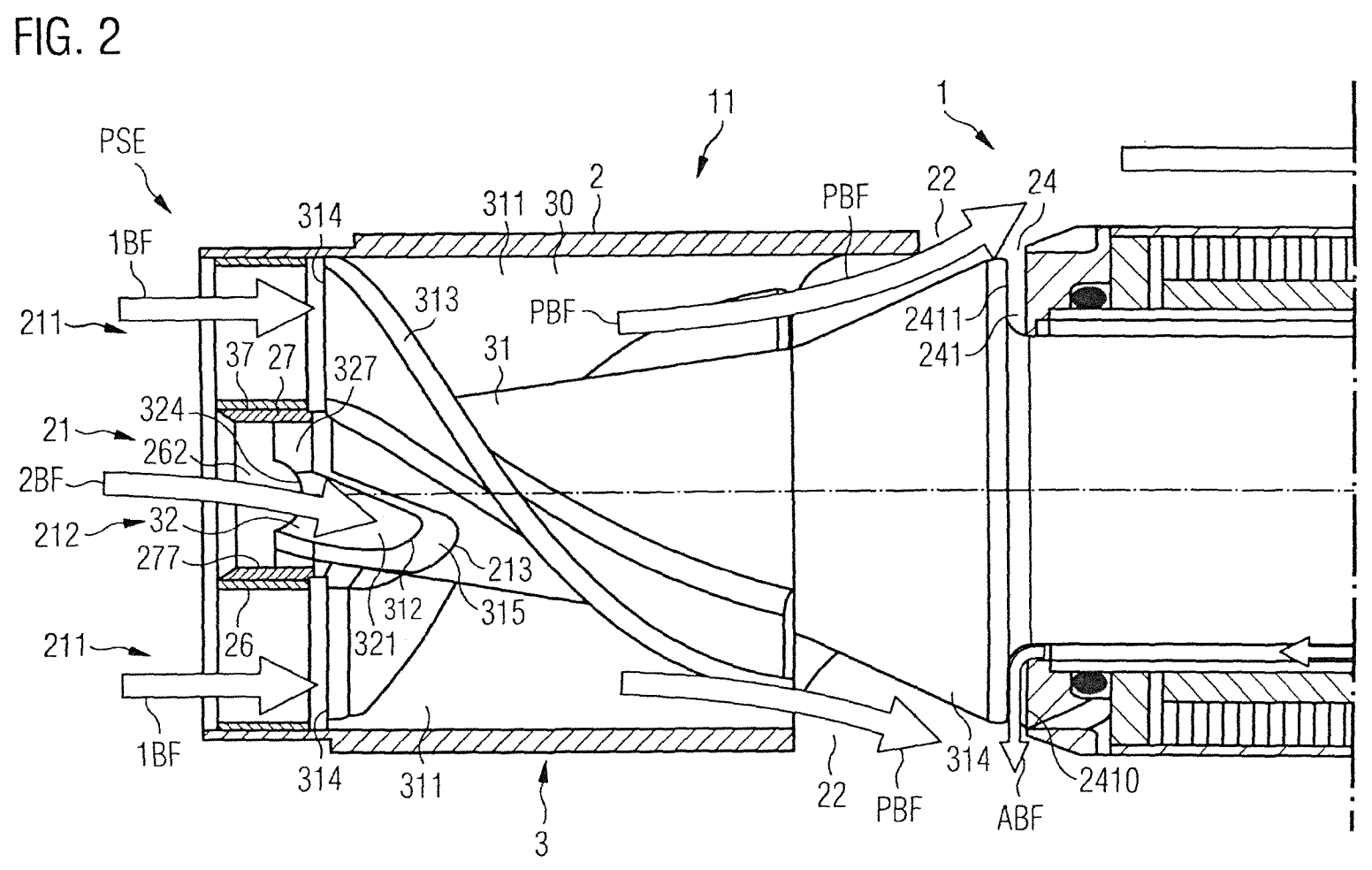
Figure 4:
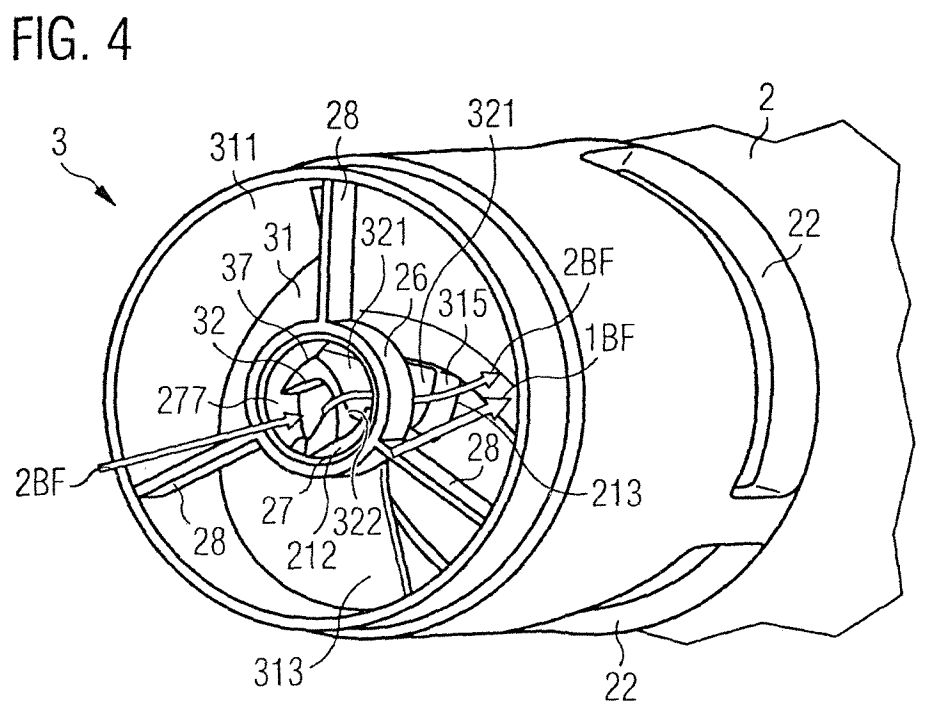
Figure 5:
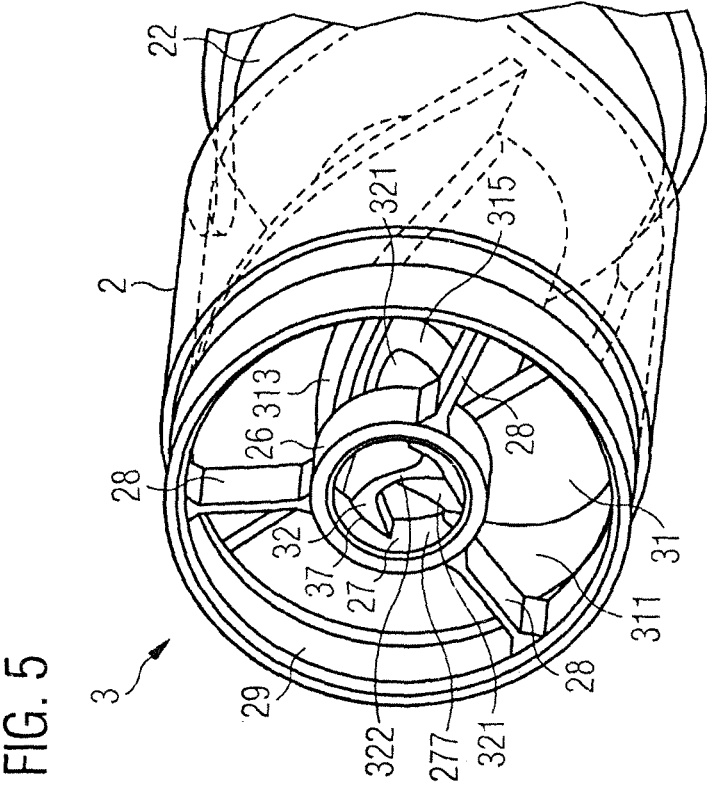
Figure 7:
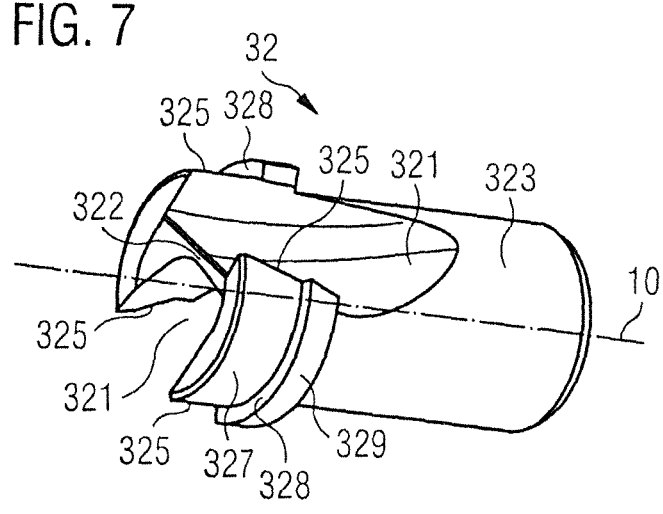
FIG. 7 shows a perspective view of an embodiment of the secondary impeller.

As can be better seen in the enlarged representation of the pump section shown in FIG. 2, together with the front perspective views depicted in FIGS. 4 and 5, the blood flow inlet 21 comprises a primary blood flow inlet 211 and a secondary blood flow inlet 212. The primary blood flow inlet 211 surrounds the secondary blood flow inlet 212. The primary blood flow inlet 211 and the secondary blood flow inlet 212 are separated by an inflow separator 26. Inside the inflow separator 26, the inflow separator 26 comprises an impeller bearing ring 27, which is separately shown in FIG. 8. Further, the pumping device 11 comprises a primary impeller 31 which has integrated therein a secondary impeller 32. The primary and secondary impellers 31, 32 are rotatable together about an axis of rotation 10. The secondary impeller 32 may, as shown in FIG. 7, have the form of an inlay and may be arranged inside a secondary impeller cavity 312 of the primary impeller 31. The secondary impeller cavity 312 is open toward a pump section end PSE of the pumping device 11. Alternatively, the primary and secondary impellers 31, 32 are integrally formed.

A primary blood flow 1BF flows from the primary blood flow inlet 211 to the primary impeller 31 outside of the inflow separator 26 to be conveyed further by the primary impeller 31 through a primary blood flow passage 30 to the primary blood flow outlet 22. A secondary blood flow 2BF flows from the secondary blood flow inlet 212 through the inflow separator 26 to the secondary impeller 32 to be conveyed further by the secondary impeller 32 through a plurality of secondary blood flow passages 321 to the primary blood flow passage 30.

Thus, a blood stream arriving at the pumping device 11 at the pump section end, preferably about almost the whole cross section of the pumping device 11, can flow into the primary and secondary blood flow inlets 211, 212 without significant deflection. Because of the central position of the secondary blood flow inlet 212, also blood from the middle of the blood stream can enter the pumping device 11 without deflection. This is advantageous because usually a blood stream is a laminar flow in which the flow velocity is greatest in the center.

The primary impeller 31 comprises primary impeller vanes 313 which extend into the primary blood flow passage 30 and between which primary impeller channels 311 are arranged. The primary impeller channels 311 have a primary pitch at a primary channel intake 314 at each end of the primary impeller channels 311 toward the pump section end PSE. The secondary impeller 32 comprises at least one and particularly exactly two secondary blood flow passages 321 in channel form, which are therefore referred to hereinafter also as secondary impeller channels 321 (see also FIG. 7). The secondary impeller channels 321 have a secondary pitch at a secondary channel intake 324 which is arranged at an upstream end of the secondary impeller channel 321. The secondary pitch is preferably the same as the primary pitch or may vary to a certain degree as long as undesirable flow conditions, such as turbulences, are prevented. At an end of the secondary impeller 32 toward a drive section end DSE, a connecting breakthrough 315 between the secondary impeller cavity 312 and one of the primary blood flow passages 311 is arranged. An end of this breakthrough 315 in the direction of the blood flow defines the secondary blood flow outlet 213. The secondary blood flow outlet 213 is arranged further radially outward in regard to the axis of rotation 10. Therefore, blood is forced outward in a radial direction by centrifugal forces caused by the rotation of the secondary impeller 32. In this way, the secondary blood flow 2BF is conveyed through the secondary blood flow inlet 212 and further through the secondary impeller channel 321 of the secondary impeller 32 and unites with the primary blood flow 1BF flowing through the primary impeller channel 311 of the primary impeller 31. In this way, a pumped blood flow PBF is formed. The pumped blood flow PBF leaves the pumping device 11 at the blood flow outlet 22.

The primary and secondary impellers 31, 32 are jointly mounted in an impeller bearing 37. They are connected via the secondary impeller cavity 312 or integrally formed as one single piece. The inflow separator 26 comprises an impeller bearing ring 27 arranged inside the inflow separator 26. An outer impeller bearing surface 277 of the impeller bearing 37 is arranged at the inside of the impeller bearing ring 27. The impeller bearing 37 further comprises an inner impeller bearing surface 327 which is arranged at an outer circumference of the secondary impeller 32.

The primary impeller 31 is fixedly connected to a tapered section 314 leading to the blood flow outlet 22. The tapered section 314 directs the pumped blood flow PBF in a direction radially outward in regard to the axis of rotation 10. The blood then reaches the blood flow outlet 22.

From the tapered section 314 in a direction toward the pump section end PSE, a drive section 4 is arranged inside the pump casing 2 of the pumping device 11, which comprises a stator 40 and a rotor 41. Between the stator 40 and the rotor 41, an axial gap 401 is arranged. In order to cool the stator 40 and the rotor 41, the axial gap 401 is blood-purged. For this, an ancillary blood flow ABF enters the drive section 4 through an ancillary blood flow inlet 23 arranged at the drive section end DSE. The blood is then conveyed by an ancillary impeller 42 through an ancillary pump gap 423 which is arranged between the ancillary impeller 42 and an inner wall of the pump casing 2. From there, the blood continues to flow into the axial gap 401. From the axial gap 401, the ancillary blood flow ABF enters a radial gap 241. At the radial outer end of the radial gap 241, an ancillary blood flow outlet 24 is arranged. The ancillary blood flow ABF flows in the axially gap 401 in a direction opposite to the pumping direction of the primary and secondary impellers 31, 32. The ancillary blood flow ABF inside the drive section 4 also flows substantially in an opposite direction to a general blood flow GBF flowing around the blood pump 1.

Figure 3:
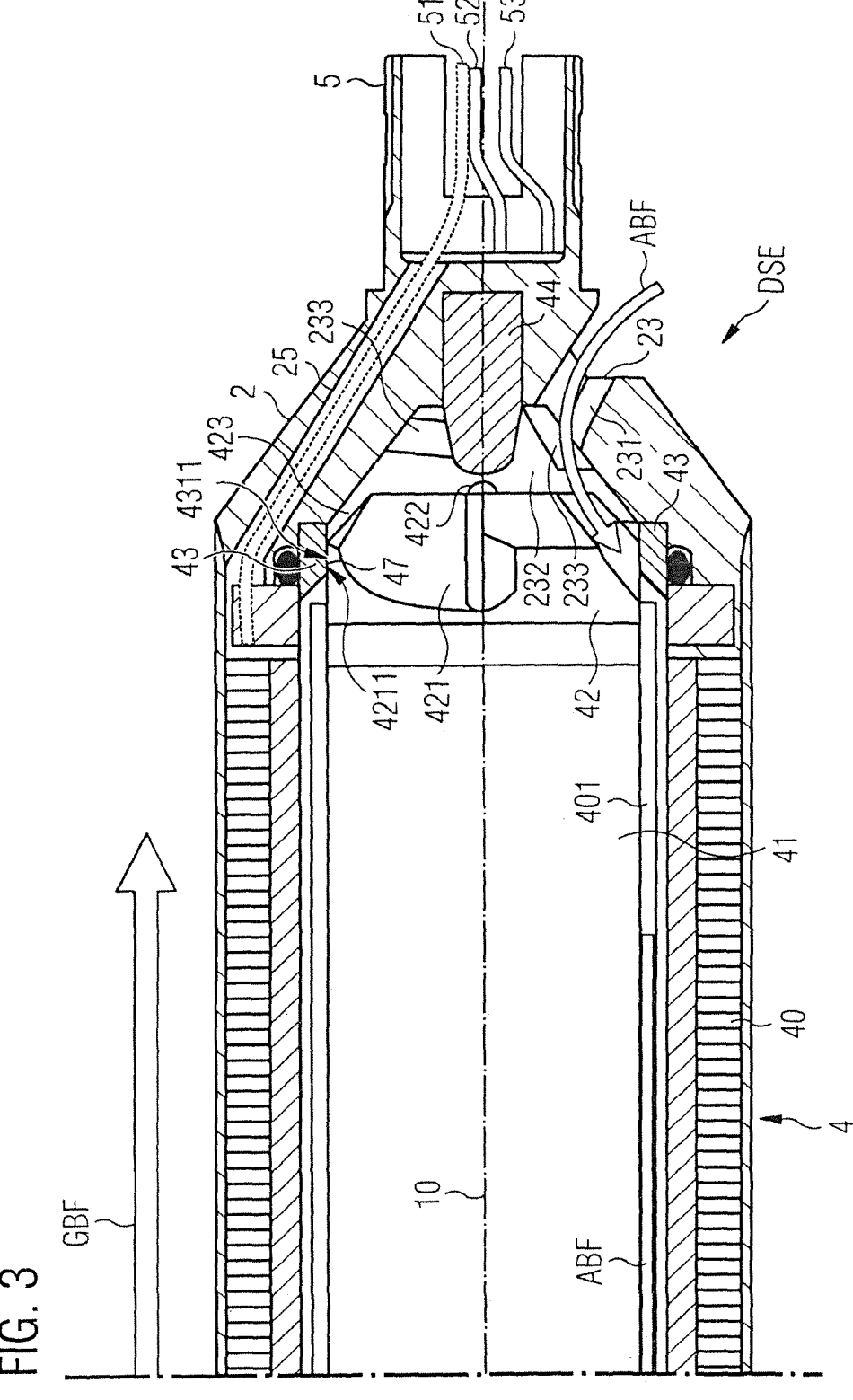
FIG. 3 shows a part of FIG. 1 with the drive section in an enlarged view.

As can be better seen in reference to the enlarged representation shown in FIG. 3, a rotor bearing ring 43 surrounds the ancillary impeller 42. The ancillary impeller 42 comprises ancillary impeller vanes 421. The ancillary impeller vanes 421 protrude in a direction of the axis of rotation 10 toward the drive section end DSE of the pumping device 11. A radial rotor bearing 47 is arranged at the drive section end DSE and comprises an outer rotor bearing surface 4211 and an inner rotor bearing surface 4311, between which an axially extending bearing gap is arranged. The outer rotor bearing surface 4311 is arranged on the rotor bearing ring 43. Blood conveyed by the ancillary impeller 42 flows through the bearing gap and further to the axial gap 401 between the rotor 41 and the stator 40. From the axial gap 401, the blood flows to a radial gap 241. The radial gap 241 extends between the tapered section 314 of the primary impeller 31 and the stator 40. An ancillary blood flow outlet 24 is arranged at the transition between the radial gap 241 and the surrounding of the pumping device 11. The ancillary blood flow outlet 24 is arranged perpendicularly to the axis of rotation 10. Here, the blood from the ancillary blood flow ABF unites with the pumped blood flow PBF from the pump section 2 and the surrounding general blood flow GBF. When the ancillary blood flow outlet 24 is, as shown, arranged close to the outer diameter of the pump casing 2 and close to the primary blood flow outlet 22, the pumped blood flow PBF and the general blood flow GBF support the drawing of blood out of the radial gap 241 because of their flow velocity. This enhances the ancillary blood flow ABF through the axial gap 401.

At a center of the ancillary impeller 42, through which the axis of rotation 10 extends, and at a side of the ancillary impeller 42 opposite to the rotor 41, a hump 422 is arranged. In a direction of the axis of rotation 10 toward the drive section end DSE and adjacent to the hump 422, a bearing pin 44 is arranged. The bearing pin 44 is connected to the pump casing 2. An axial bearing surface of the bearing pin 44 toward the ancillary impeller 42 has a convex shape. The axis of rotation 10 runs through an apex of the axial bearing surface of the bearing pin 44 and through an apex of the axial bearing surface of the hump 422. In this way, the bearing pin 44 interacts with the hump 422 and forms a thrust bearing in order to transmit axial forces in regard to the axis of rotation between the hump 422 and the bearing pin 44, wherein the aforementioned parts are rotatable relative to each other. Obviously, the contact surface is small, such that rotational friction is low.

The drive section end of the blood pump 1 comprises one or more, preferably three, ancillary inlet through-holes 231. The ancillary inlet through-holes 231 extend from the ancillary blood flow inlet 23 to an ancillary impeller cavity 232 in which the ancillary impeller 42 is arranged. Thus, the blood flows from the ancillary blood flow inlet 23 to the ancillary impeller 42 via the ancillary inlet through-hole 231.

At least one wire through-hole 25 is arranged at the drive section end DSE of the pumping device 11. The wire through-holes 25 may extend from the catheter 5 to the stator 40. Preferably, three wire through-holes 25 are arranged about the axis of rotation 10. Between two ancillary inlet through-holes 231, one wire through-hole 25 may be arranged. In a wire through-hole 25, at least one supply line 51, 52 and/or 53 may extend to be connected to the stator 40. Preferably, as shown, the supply wires 51, 52 and/or 53 extend through the inside of the catheter 5 to the outside of the patient's body. The supply wires 51, 52 and/or 53 run from the catheter 5 to the stator 40 without contact to blood.

FIG. 4 shows a perspective front view on the pump section end PSE of the pump section 3. As is shown, the secondary impeller 32 is arranged inside the impeller bearing ring 27. The impeller bearing ring 27 is arranged inside the inflow separator 26. Alternatively to this embodiment, the additional impeller bearing ring 27 can be omitted such that the outer impeller bearing surface 277 is formed by the inflow separator 26. Here, the inflow separator 26 is mounted between the primary blood flow 1BF and the secondary blood flow 2BF by three struts 28. It is shown that the secondary blood flow 2BF flows into the secondary impeller 32 through the secondary blood flow inlet 212 which is arranged at an inflow into the impeller bearing ring 27. In the secondary impeller 32, the blood flows along the secondary impeller channel 321 and through the through-opening 315 to the secondary blood flow outlet 213. Here, the secondary blood flow 2BF unites with the primary blood flow 1BF to form the pumped blood flow PBF.

FIG. 5 shows the pump section end PSE of the pump section 3 in a perspective view, wherein the pump casing 2 is shown in transparency. The through-opening 315 and the secondary blood flow outlet 213 are arranged between two primary impeller vanes 313. As shown, the struts 28 are connected by an outer strut connection ring 29. The strut connection ring 29 is arranged inside an inner circumferential surface of the pump casing 2 at the pump section end PSE. The impeller bearing ring 27 is supported by the struts 28. It is conceivable to manufacture the strut connection ring 29 and the struts 28 as one piece. Preferably, also the impeller bearing ring 27 is a part of this piece. Said piece may also be formed in one piece with the pump casing 2.

Figure 6:
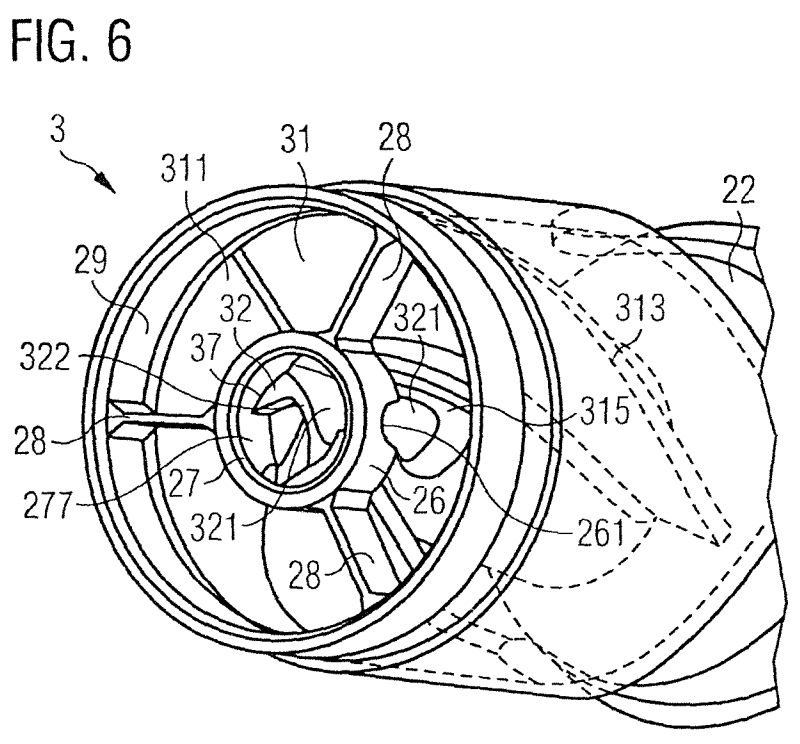
Figure 8:
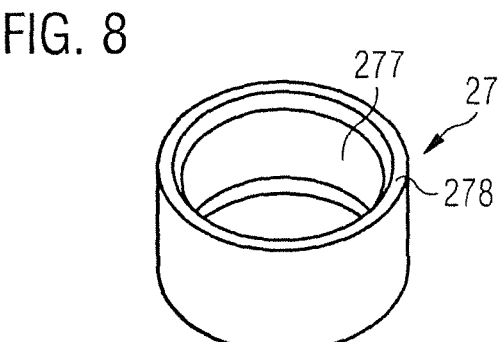
FIG. 8 shows a perspective view of a separator ring of the first embodiment of the blood pump.
Figure 9:
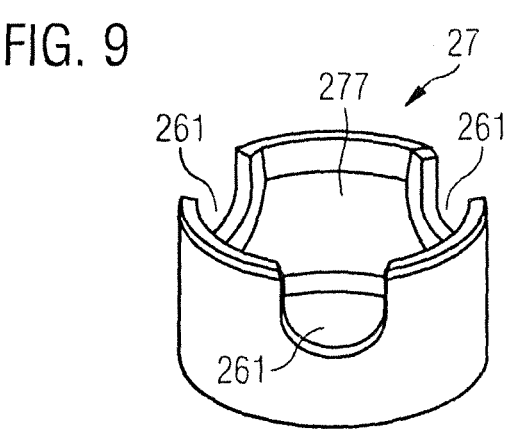
FIG. 9 shows a perspective view of a separator ring of the second embodiment of the blood pump.

FIG. 6 shows a perspective view of the pump section end PSE of the pump section 3 in which the pump casing 2 is shown in transparency different from the embodiment shown in FIGS. 3 to 5, the inflow separator 26 comprises at least one, preferably three, cut-outs 261 at a downstream end of the inflow separator 26. The cut-out 261 is arranged between two struts 28. The impeller bearing ring 27 is part of or fixedly connected to the inflow separator 26, and the cut-out 261 also extends through the impeller bearing ring 27. Due to the cut-out 261, the secondary impeller channel 321 has an increased cross section when it aligns with the cut-out 261 during rotation of the secondary impeller. The secondary impeller 32 extends inside the impeller bearing ring 27 in a direction toward the pump section end PSE maximally up to an end of the cut-out 261. This has the effect that, in operation, an edge of the cut-out 261 runs over the inner impeller bearing surface 327 and removes blood clots at the beginning of their formation or preferably prevents their formation, since the mating part of the rotating axial thrust bearing surface 328 is in direct blood contact at the cut-out 261. This helps to avoid stagnant blood within the axial thrust bearing. Also the inner impeller bearing surface 327 has edges 325, as can be seen in FIG. 7, which have the effect to remove blood clots from the outer impeller bearing surface 277 (FIGS. 8 and 9).

FIG. 7 shows the secondary impeller 32 in detail in a perspective view. There, the secondary impeller 32 is configured as an inlay and has roughly the form of a cylinder. It may be made of different material as the primary impeller 31, for instance of a ceramic material. The inlay comprises a cylindrical section 323 which is arranged inside the secondary impeller cavity 312 of the primary impeller 21. A circumferential protrusion 329 forms an axial stop for the secondary impeller 32 in the secondary impeller cavity 312. The inner impeller bearing surface 327 is arranged at an outer circumference of the secondary impeller 32. Two secondary impeller channels 321 are arranged at the end of the secondary impeller 32 toward the pump section end PSE. The secondary impeller channels 321 have their largest cross section at the upstream end of the secondary impeller 32. Thus, the channels 321 decrease in cross section away from the blood flow inlet 21. In this way, blood is directed from a mainly axial direction to an axial-radial direction when it flows through the secondary impeller channel 321.

The secondary impeller channels 321 are arranged asymmetrically in regard to the axis of rotation 10 of the secondary impeller 32. At an end of the secondary impeller 32 directed toward the blood flow inlet 21, the axis of rotation 10 extends through one of the secondary impeller channels 321. In this way, the center of rotation, which is located at the axis of rotation 10, does not coincide with a solid part of the secondary impeller 32. This has the advantage that blood clotting at the center of rotation, where no differential velocity to neighboring blood flow is present, can be avoided.

At the transition between the secondary impeller channels 321 and the inner impeller bearing surface 327, edges 325 are arranged. As mentioned above, such edges 325 serve to push away formations of blood clotting on the outer impeller bearing surface 277. The inner impeller bearing surface 327 provides an inner surface of a radial bearing at the pump section end PSE. The secondary impeller 32 further comprises an axial impeller bearing surface 328. It is arranged at the circumferential protrusion 329. The axial impeller bearing surface 328 forms a part of the above-mentioned axial stop or axial thrust bearing. The axial stop may be configured as an axial bearing which is capable of transmitting forces from the secondary impeller 32 to the bearing ring 27 during rotation of the impeller. The axial bearing is necessary to counter the axial force which stems from the purging action of the impeller.

FIG. 8 shows an enlarged view of the impeller bearing ring 27. The outer impeller bearing surface 277 is arranged at the inside of the impeller bearing ring 27. The impeller bearing ring 27 comprises an axial bearing ring surface 278. As shown, the axial bearing ring surface 278 may be arranged at an axial end of the impeller bearing ring 27.

FIG. 9 shows a perspective view of an impeller bearing ring 27 according to a further embodiment which differs from the embodiment shown in FIG. 8 in that it comprises the cut-outs 261, as previously mentioned, which are arranged at a downstream end of the impeller bearing ring 27. The number of cut-outs 261 preferably matches the number of struts 28.

Figure 10:
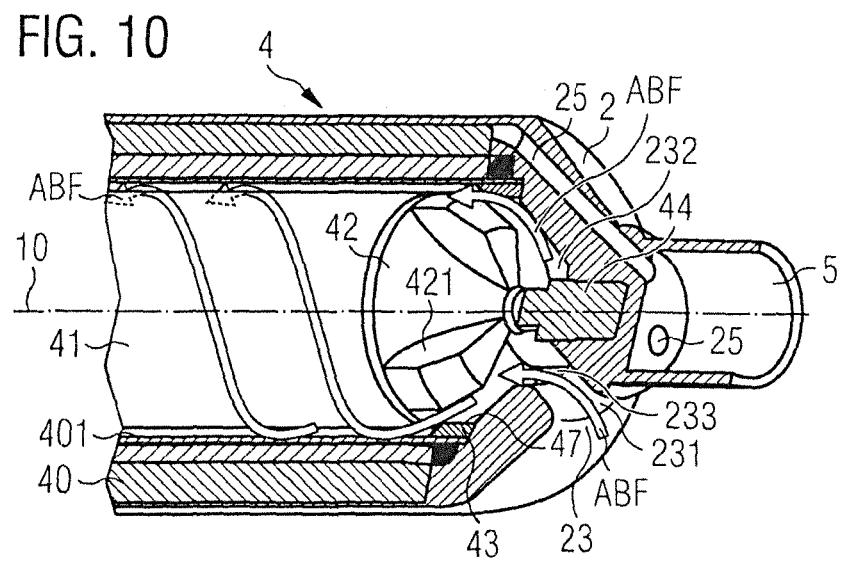
FIG. 10 shows a cross section of the drive section end of the blood pump in a perspective view depicting an ancillary impeller.

FIG. 10 shows a perspective view of a cross section through the drive section end DSE of the drive section 4. Rotating parts are not shown cut. As shown, the ancillary blood flow ABF enters the pump casing 2 at the ancillary blood flow inlet 23. The ancillary impeller 42 accelerates the blood, which continues to flow into the axial gap 401. As is shown by the arrow ABF inside the axial gap 401, the blood does not flow directly in the direction of the axis of rotation 10, but rather has a strong circumferential flow component so that it flows along the axial gap 401 along helices.

FIG. 11 shows a perspective view of an end of the rotor 41 at the drive section end DSE of the pumping device 11. The ancillary vanes 421 of the ancillary impeller 42 are clearly recognizable, and they extend straight in a radial direction. The ancillary impeller vanes 421 provide, at their outer circumference, the inner rotor bearing surface 4211 of the radial rotor bearing 47. Further, the ancillary impeller vanes 421 each have a chamfer 4212. This chamfer 4212 is advantageous in order to build a tapered drive section end DSE of the pumping device 11 as shown in FIG. 10. Further, the ancillary impeller vanes 421 comprise radially extending end surfaces 4214 at an axial end of the secondary impeller 42. A hump 422 is formed at the center of the axial end of the secondary impeller 42. The hump 422 interacts with the bearing pin 44, as shown in FIG. 10.

Figure 11A:
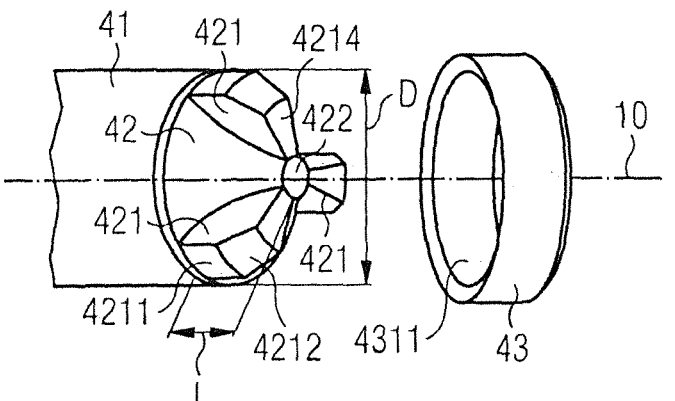
FIG. 11A shows a perspective view of the ancillary impeller and of a rotor bearing ring.
Figure 11B:
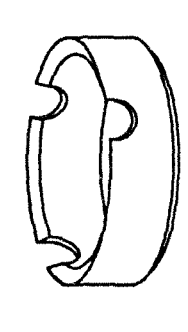
FIG. 11B shows a perspective view of a rotor bearing ring having cut-outs.

FIG. 11A further shows the rotor bearing ring 43 to be arranged around the inner rotor bearing surface 4211 of the secondary impeller 42. The outer rotor bearing surface 4311 of the rotor bearing ring 43 forms the rotor bearing 47 together with the inner rotor bearing surface 4211 of the ancillary impeller 42. The ancillary impeller 42 has an axial length L and a diameter D. Alternatively, as shown in FIG. 11B, the rotor bearing ring 43 may have cut-outs with a form, function and arrangement similar to the cut-outs 261 of above-described impeller bearing ring 27.

Figure 12:
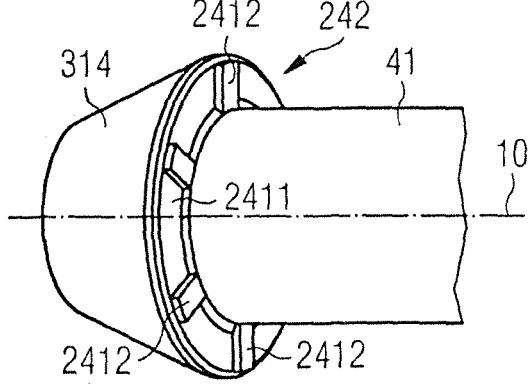
FIG. 12 shows a perspective view of a tertiary impeller of the first or the second embodiment.

FIG. 12 shows in a perspective view an end of the rotor 41 connected to the tapered section 314 of the primary impeller 31. A tertiary impeller 242 is arranged between the tapered section 314 and the pump section end of the rotor 41, and extends radially from an outer diameter of the rotor 41 to an outer diameter of the tapered section 314 to form a shoulder. An axial plane of this shoulder forms a rotatable wall 2411 of the radial gap 24. From the rotatable wall 2411, the tertiary impeller vanes 2412 project toward the drive section end DSE of the pumping device 11. Preferably, the tertiary impeller vanes 2412 extend axially along the axis of rotation 10. Particularly, the tertiary impeller vanes 2412 are straight and extend in a radial direction relative to the axis of rotation 10. Further, in the alternative, the tertiary impeller vanes 2412 can be omitted (not shown).

The invention claimed is:

1. An intravascular blood pump, comprising a pumping device with a pump section and a drive section, wherein:
   the pump section comprises a pump casing having a primary blood flow inlet and a primary blood flow outlet hydraulically connected by a primary passage and the drive section comprises a stator and a rotor rotatable about an axis of rotation and configured to rotate a primary impeller, the primary impeller being configured to convey a primary blood flow from the primary blood flow inlet to the primary blood flow outlet along the primary passage in a first direction,
   the drive section further comprises an ancillary blood flow inlet and an ancillary blood flow outlet hydraulically connected by an ancillary passage extending through an axial gap between the rotor and the stator and an ancillary impeller arranged at a drive section end (DSE) of the rotor and rotatable about the axis of rotation along with the rotor, the ancillary impeller comprising one or more ancillary impeller vanes configured to convey an ancillary blood flow from the ancillary blood flow inlet to the ancillary blood flow outlet along an ancillary passage in a second direction toward a pump section end (PSE) of the pumping device, the first direction being opposite to the second direction, the rotor is mounted in a blood-purged radial sliding rotor bearing with an inner rotor bearing surface and an outer rotor bearing surface, and the ancillary impeller forms the inner rotor bearing surface of the radial sliding rotor bearing.

2. The intravascular blood pump according to claim 1, wherein the inner rotor bearing surface and the rotor have a common outer diameter.

3. The intravascular blood pump according to claim 1, wherein the ancillary impeller is a radially or a radially-axially delivering impeller.

4. The intravascular blood pump according to claim 1, wherein the ancillary impeller vanes each have an outer circumferential surface and wherein the inner rotor bearing surface is formed by the outer circumferential surfaces of at least two of the ancillary impeller vanes.

5. The intravascular blood pump according to claim 1, wherein at least one of the one or more ancillary impeller vanes protrudes axially from the ancillary impeller.

6. The intravascular blood pump according to claim 1, wherein at least one of the one or more ancillary impeller vanes extends radially from the ancillary blood flow inlet at least up to the axial gap.

7. The intravascular blood pump according to claim 1, wherein at least one of the one or more ancillary impeller vanes extends along a radial direction relative to the axis of rotation.

8. The intravascular blood pump according to claim 1, wherein at least one of the one or more ancillary impeller vanes forms an ancillary pump gap with an inner wall of the pump casing.

9. The intravascular blood pump according to claim 4, wherein the outer circumferential surface of the at least two of the ancillary impeller vanes is slanting in a circumferential direction so as to form a hydrodynamic sliding rotor bearing.

10. The intravascular blood pump according to claim 1, wherein the inner rotor bearing surface comprises a radially protruding bulge with an apex of the bulge extending in a circumferential direction.

11. The intravascular blood pump according to claim 1, wherein the inner rotor bearing surface is made of ceramic material.

12. The intravascular blood pump according to claim 11, wherein the ancillary impeller is an integral piece of ceramic material.

13. The intravascular blood pump according to claim 1, wherein a part of the pumping device forming the outer rotor bearing surface of the radial sliding rotor is a rotor bearing at least partially surrounding the ancillary impeller.

14. The intravascular blood pump according to claim 13, wherein the outer rotor bearing surface is made of ceramic material.

15. The intravascular blood pump according to claim 14, wherein a part of the pumping device forms the outer rotor bearing surface.

16. The intravascular blood pump according to claim 1, comprising an axial rotor bearing or an axial-radial rotor bearing having an axial or an axial-radial rotor bearing surface, respectively, which is arranged at the ancillary impeller.

17. The intravascular blood pump according to claim 16, wherein at least the axial or axial-radial rotor bearing surface of the ancillary impeller is made of ceramic material.

18. The intravascular blood pump according to claim 11, wherein the ceramic material is silicon carbide.

19. The intravascular blood pump according to claim 1, wherein an axial length of the ancillary impeller is smaller than a maximum outer diameter of the ancillary impeller.

20. The intravascular blood pump according to claim 1, wherein the primary impeller and the ancillary impeller are arranged on opposite sides of the rotor.

21. The intravascular blood pump according to claim 1, wherein a radially outer edge of the one or more of the ancillary impeller vanes is chamfered.

22. The intravascular blood pump according to claim 1, wherein the ancillary blood flow outlet is arranged outside the primary passage.

23. The intravascular blood pump according to claim 1, wherein the ancillary blood flow inlet comprises a plurality of ancillary inlet through-holes arranged about the axis of rotation.

24. The intravascular blood pump according to claim 23, wherein, in an interspace between two of the ancillary inlet through-holes, a wire channel for an electric supply wire for the drive section is arranged.

25. The intravascular blood pump according to claim 23, wherein the axial gap has an inlet arranged for blood to flow into the axial gap, and wherein an internal end of at least one of the plurality of ancillary inlet through-holes is arranged further radially inward than a radially innermost section of the inlet into the axial gap.

26. The intravascular blood pump according to claim 1, wherein the pumping device comprises a tertiary impeller arranged for drawing the ancillary blood flow through the ancillary passage.

27. The intravascular blood pump according to claim 26, wherein the tertiary impeller is rotatable about the axis of rotation along with the rotor.

28. The intravascular blood pump according to claim 27, wherein the ancillary blood flow outlet is arranged at a radial gap between the primary impeller and the stator.

29. The intravascular blood pump according to claim 28, wherein the ancillary blood flow outlet is arranged such that, in operation, a pumped blood flow (PBF) leaving the primary blood flow outlet passes the ancillary blood flow outlet.

30. The intravascular blood pump according to claim 28, wherein a rotatable wall of the radial gap is rotatable along with the rotor.

31. The intravascular blood pump according to claim 30, wherein a stationary wall of the radial gap opposite to the rotatable wall of the radial gap is mechanically connected to the stator.

32. The intravascular blood pump according to claim 30, wherein the tertiary impeller is arranged in the radial gap.

33. The intravascular blood pump according to claim 32, wherein the tertiary impeller comprises at least one tertiary impeller vane which protrudes from the rotatable wall of the radial gap.

34. The intravascular blood pump according to claim 32, wherein an inflow to the tertiary impeller is arranged at an outflow end of the axial gap.

35. The intravascular blood pump according to claim 1, wherein the first direction of the ancillary blood flow is helical along the ancillary passage.

* * * * *